(12) United States Patent
Kuczynski (10) Patent No.: US 7,736,367 B2
(45) Date of Patent: Jun. 15, 2010

(54) RIBBED FEMORAL CUTTING GUIDE

(75) Inventor: John Douglas Kuczynski, Wayne, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 328 days.

(21) Appl. No.: 10/860,746

(22) Filed: Jun. 3, 2004

(65) Prior Publication Data
US 2005/0273113 A1  Dec. 8, 2005

(51) Int. Cl.
*A61B 17/58* (2006.01)
(52) U.S. Cl. ................. 606/86 R; 606/87; 606/88
(58) Field of Classification Search ........... 606/86, 606/86 R, 96, 79–82, 84, 87–89, 102, 104
See application file for complete search history.

(56) References Cited

U.S. PATENT DOCUMENTS

| | | | | |
|---|---|---|---|---|
| 3,621,573 A | * | 11/1971 | Summers | 30/287 |
| 4,474,177 A | | 10/1984 | Whiteside | |
| 4,487,203 A | | 12/1984 | Androphy | |
| 4,502,483 A | | 3/1985 | Lacey | |
| 4,524,766 A | | 6/1985 | Petersen | |
| 4,653,488 A | | 3/1987 | Kenna | |
| 4,833,956 A | * | 5/1989 | Roberts | 83/56 |
| 4,926,847 A | * | 5/1990 | Luckman | 606/88 |
| 5,053,037 A | | 10/1991 | Lackey | |
| 5,122,144 A | | 6/1992 | Bert et al. | |
| 5,245,797 A | * | 9/1993 | Milkie | 451/354 |
| 5,364,401 A | * | 11/1994 | Ferrante et al. | 606/84 |
| 5,454,816 A | | 10/1995 | Ashby | |
| 5,624,444 A | * | 4/1997 | Wixon et al. | 606/88 |
| 5,653,714 A | * | 8/1997 | Dietz et al. | 606/87 |
| 6,558,391 B2 | * | 5/2003 | Axelson et al. | 606/88 |
| 6,575,980 B1 | * | 6/2003 | Robie et al. | 606/88 |
| 6,740,092 B2 | * | 5/2004 | Lombardo et al. | 606/88 |
| 6,964,075 B1 | * | 11/2005 | Iannacone, Jr. | 7/103 |

* cited by examiner

*Primary Examiner*—Eduardo C Robert
*Assistant Examiner*—Tara R George
(74) *Attorney, Agent, or Firm*—Lerner, David, Littenberg, Krumholz & Mentlik, LLP (57) ABSTRACT

A cutting block includes a body having at least three sections spaced in the anterior-posterior direction. Each section has a proximally facing surface for being placed adjacent to the distally facing surface of the femur. The block includes a distally facing surface with a rib connecting the at least three sections. The rib extends outwardly from the distally facing surface of each of the sections of the cutting block. The rib spaces the sections to form a guide slot between adjacent sections for receiving a saw blade. The rib has a proximally facing surface spaced distally of the distal surface of the cutting block adjacent the slots.

25 Claims, 6 Drawing Sheets

RIBBED FEMORAL CUTTING GUIDE

BACKGROUND OF THE INVENTION

The present invention relates generally to the implant of prosthetic joints and pertains, more specifically, to the preparation of the distal femur for the implantation of a femoral knee prosthesis, utilizing a femoral cutting guide to assist in establishing the surfaces necessary for locating and securing the prosthesis in place on the femur. More particularly, it relates to a cutting guide which is light weight, strong and easy to manufacture.

The implant of a prosthetic knee joint requires that the distal femur be prepared to receive the femoral component of the knee prosthesis by cutting the bone of the femur to establish accurately located surfaces. Upon implantation, the femoral component will rest on these surfaces. As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Various resection guides are available to the surgeon for assisting in guiding a saw blade to make the femoral cuts which establish the desired surfaces. These guides usually have guide surfaces for making four resections and are located and secured on the distal femur, upon an already resected transverse surface on the distal femur. Typically, surfaces are provided for guiding the saw blade during the execution of an axially directed anterior femoral cut, an axially directed posterior femoral cut, an anterior chamfer cut and a posterior chamfer cut, all specifically related to the size of the femoral knee prosthesis to be implanted and to the position and orientation of the femoral knee prosthesis on the distal femur. This type of cutting block is known as a four in one cutting block. Such blocks are shown in U.S. Pat. Nos. 4,892,093, 5,012,909, 5,364,401, 5,683,397 and 6,258,095. The appropriate location of a femoral cutting guide, then, generally requires the use of well known instruments and alignment techniques to determine the size of the femoral knee prosthesis which will be implanted at an implant site in a particular recipient, and to locate the corresponding femoral cutting guide appropriately on the transverse distal femoral surface for proper placement of the femoral knee prosthesis upon implant at the implant site.

SUMMARY OF THE INVENTION

It is an object of the invention to provide a femoral cutting guide for resection of the distal femur which is light weight, strong and easy to manufacture. It is a further object of the invention to provide a femoral cutting guide which can dissipate any heat generated during the resection of the distal femur utilizing a saw blade guided by the block.

It is yet an additional object of the invention to provide continuous cutting surfaces through the medial-lateral extent of the block for supporting a flat or planar saw blade. These and other objects of the invention are achieved by a cutting block which is mountable on a distally facing surface of a femur for guiding a saw blade making bone cuts on the distal femur. A cutting block includes a body having at least three sections spaced in the anterior-posterior direction. Each section has a proximally facing surface for being placed adjacent to the distally facing surface of the femur. The block includes a distally facing surface with a rib connecting the at least three sections. The rib extends outwardly from the distally facing surface of each of the sections of the cutting block. The rib spaces the sections to form a guide slot between adjacent sections for receiving a saw blade. The rib has a proximally facing surface spaced distally of the distal surface of the cutting block adjacent the slots.

The guide slots may be formed at anterior/posterior angles to the proximal-distal direction of the femur for forming anterior and posterior chamfer cuts on a distal femur which angle is normally 45°. The guide slots may also be formed at an anterior-posterior angle to the proximal-distal direction of the femur at a lesser angle for forming the anterior and posterior cuts on the femur. Preferably, the proximally facing surfaces of each of the at least three sections are coplanar with the coplanar surfaces aligned and adapted to contact a planar resected distal surface of the femur. The central section of the three sections may include a pair of proximally extending pins for extending into the distal femur to help locate and attach the cutting block to a prepared distal femur. Preferably, only a single centrally located rib is located on the distal surface of the cutting block, however, it may be possible to use ribs located adjacent the medial and lateral sides of the block or even three ribs with one located centrally and two adjacent the sides of the block.

The cutting block is preferably made of metal such a stainless steel by starting with a solid rectangular block and using wire electrode discharge machining (EDM) to form the complex shape of the block and the slots. This type of machining utilizes a computer controlled machine which can be programmed to orient the block for multi-axis movement with respect to the electronic of the EDM machine. Such a machine is sold by MITSUBISHI model FX 20 wire EDM The electrode is programmed for movement to cut hollow cross-sections through the anterior and posterior sections of the block and to form the cutting slots and machine the rib so that it is connected to each of the at least three sections and spaced distally therefrom in the area of the slots to allow the unencumbered utilization of a saw blade throughout the slot surface.

In the preferred cutting block, the rib may be attached to four or even five sections with the outermost sections being either machined or drilled to have a plurality of bores extending in the anterior-posterior direction and extending from the medial side of the block across to the lateral side. The next most proximal and distal section would then be hollowed using EDM. The hollowed bores and hollowed cross-section of the block allows heat generated during movement of the saw blade across the guide surfaces to be quickly dissipated. This is especially so if a saline solution is used to lubricate the saw blade and cutting block during the resection and operation. The saline solution can flow into and out of the open bores and cross-sections. In addition, since the anterior-posteriorly extending bores in the anterior most and posterior most sections intersect one side of the cutting surface formed by the anterior or posterior chamfer saw blade slot this results in less heat being initially generated.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 3:
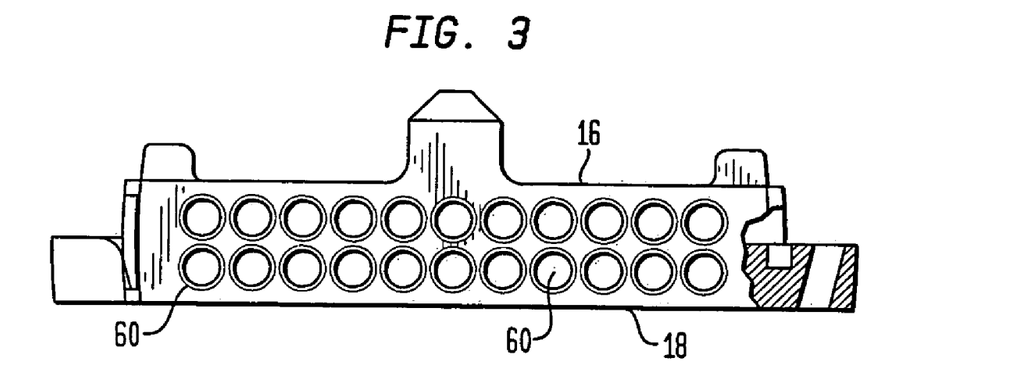
FIG. 3 is a bottom view of the cutting block shown in FIG. 1.
Figure 4:
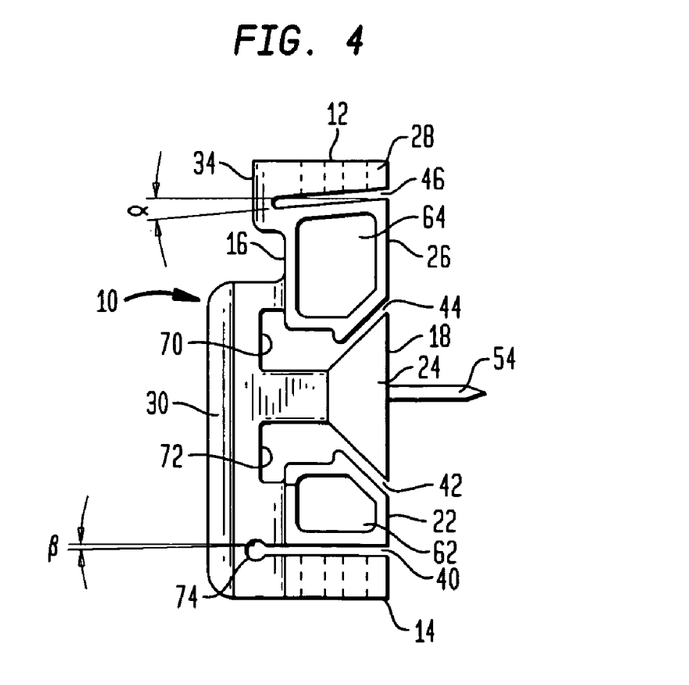
FIG. 4 is a side view of the cutting block shown in FIG. 1.
Figure 5:
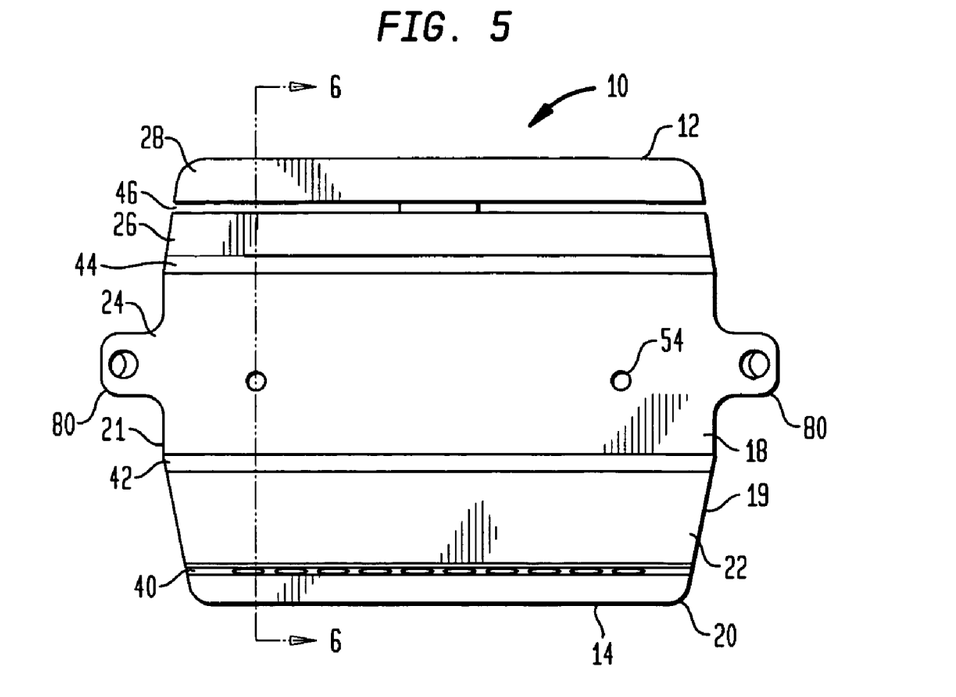
FIG. 5 is a plan view of the posteriorly facing surface of the cutting block shown in FIG. 1.

Referring to the figures, there is shown a cutting block generally denoted as 10 having an anterior surface 12, a posterior surface 14, a distal surface 16 and side surfaces 19 and 21. As seen in FIGS. 3, 4 and 5, cutting block 10 includes a proximally facing surface 18.

Figure 1:
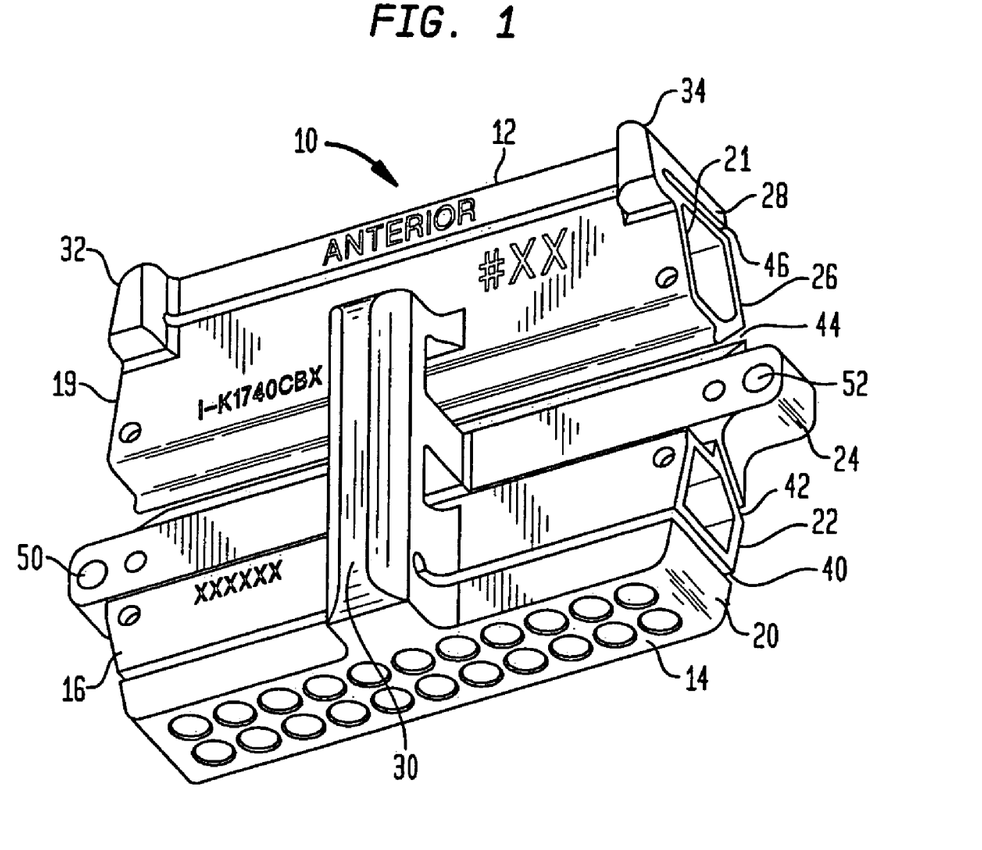
FIG. 1 is an isometric view of a distally facing cutting block of the present invention.
Figure 2:
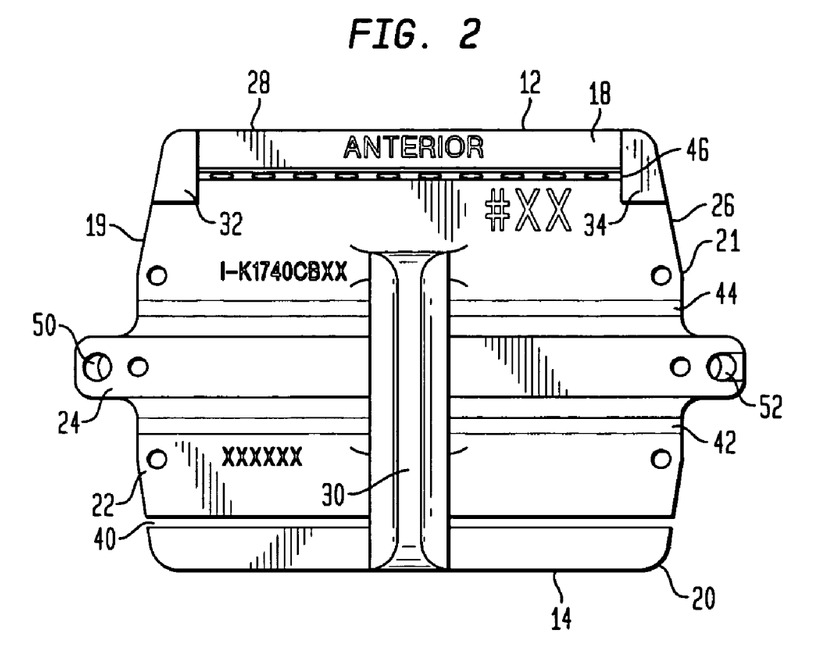
FIG. 2 is a plan view of the distal surface of the cutting block shown in FIG. 1.

Referring to FIGS. 1 and 2, it can be seen that in the preferred embodiment, cutting block 10 includes five sections 20, 22, 24, 26 and 28 starting from posterior surface 14 through anterior surface 12. In the preferred embodiment, a rib 30 is formed integral with sections 20, 22, 24 and 26. In the preferred embodiment, section 28 is made integral with section 26 by a pair of extensions 32 and 34 located on the medial and lateral sides of the block. Note that which extension 32 or 34 is on the medial or lateral side of block 10 depends on whether the cutting block is being used on a left or right knee. Thus, when used on the right knee, extension 34 would be placed medially. On the left knee it would be placed on the lateral side of the femur.

In the preferred embodiment, saw blade slots 40, 42, 44 and 46 separate sections 20, 22, 24, 26 and 28. Slot 40 is oriented to make the posterior cut on the femur and slot 46 is oriented to make the anterior cut on the femur. Slots 42 and 44 are typically at 45° angles to the distal surface of the femur and slot 42 is used to make the posterior chamfer cut and slot 44 is used to make the anterior chamfer cut.

Cutting block 10 may also include a hole 50 and a hole 52 which are used to allow block 10 to be pinned to the medial and lateral sides of the femur. In addition, if desired, additional holes extending between surfaces 16 and 18 may be utilized for affixing block 10 to the femur. As best seen in FIG. 4, a pin or pair of pins 54 may be made integral with block 10 and extend outwardly from proximally facing surface 18 to provide further fixation on the distal end of the femur.

Figure 6:
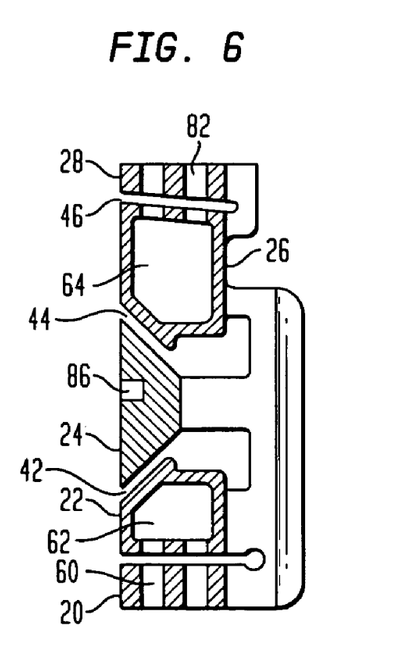
FIG. 6 is a cross-sectional view along the lines 6-6 of FIG. 5.

Referring to FIG. 3, there is shown the bottom view of surface 14 of the cutting block 10. In the preferred embodiment, surface 14 includes a plurality of holes 60 which extend in the posterior to anterior direction within section 20 all the way across the width of the cutting block and, in the preferred embodiment, holes 60 intersect slot 40. As will be discussed below with regard to the manufacturing process, these holes may be either drilled or made using wire EDM during fabricating the block. In the preferred embodiment, the holes 60 extend in a pair of rows for the entire medial and lateral width of section 20. Holes 60 not only serve to lighten the block but also allow cutting fluid to exit slot 20, thus removing any heat during use of a saw blade within slot 20. In addition, since the anterior facing surface of slot 20 is not continuous, less heat is generated by the oscillation of a typical oscillating saw blade. Likewise, as shown in FIGS. 4 and 6, section 28 of block 10 includes holes 60' which are preferably drilled through section 28 to intersect slot 46.

Referring to FIG. 4, there is shown a side view of the preferred cutting block 10 in which it can be seen that sections 22 and 26 have hollowed interiors 62 and 64 respectively to again lighten the cutting block. In the preferred embodiment, the hollow portions 62 and 64 are parallel to the outer surfaces 16 and 18 and slots 44 and 46 so as to form walls of uniform thickness. As shown in FIG. 4, the preferred central portion 24 is solid although such could also be hollowed out. It can be seen that rib 30 has a pair of proximally facing surfaces 70 and 72 which are spaced distally from distally facing surface 16 of sections 22, 24 and 26. In addition, slot 40 extends distally from proximally facing surface 18 into rib 30 and, in the preferred embodiment, includes an expanded part circular portion 74. In the preferred embodiment, posterior chamfer saw guide slot 40 is oriented posteriorly at a slight angle β with respect to the planar distally facing surface of the femur. In the preferred embodiment, β is about 1°. Likewise, anterior chamfer slot 46 is oriented anteriorly and angle α which, in the preferred embodiment, is 4°. As previously stated, slots 42 and 44 are preferably angled at approximately 45° to the plane of surface 18. Of course, all these angles can vary to match the design of the prosthetic femoral component to be implanted.

By spacing surfaces 70, 72 distally of surface 16, this allows the saw blade to traverse the entire guide surface including the central portion of the block without being obstructed. While rib 30 is shown centrally located between sides 19 and 21 of block 10, it would be possible to locate a pair of ribs adjacent each side 19, 21. Likewise, it would be possible to include section 28 integral with rib 30, although in the preferred embodiment, extensions 32 and 34 integrally couple section 28 to section 26. As long as the proximally facing surface of rib 30 is spaced from distal surface 16 of block 10 the slot surfaces remain unobstructed which facilitates the sawing operation with a typical flat blade saw.

Referring to FIG. 5, there is shown that holes 50 and 52 are preferably located on bosses 80 extending from sides 19 and 21 of block 10. Referring to FIG. 6, there is shown a cross-sectional view of the cutting block 10 along lines 6-6 of FIG. 5. The cross-sectional view shows holes 60 in the posterior most section 20 as well as holes 60' located in section 28. As can be seen in FIG. 6, in the preferred embodiment, holes 60, 60' extend into sections 22, 26 extending into the interior of hollowed portion 62, 64 respectively. Likewise, holes 60' extend across the cutting slot 46 and into the hollow interior 64 of section 26. Central portion 24 also includes a recessed bore 86 which is used for mounting pins 54.

Figure 7:
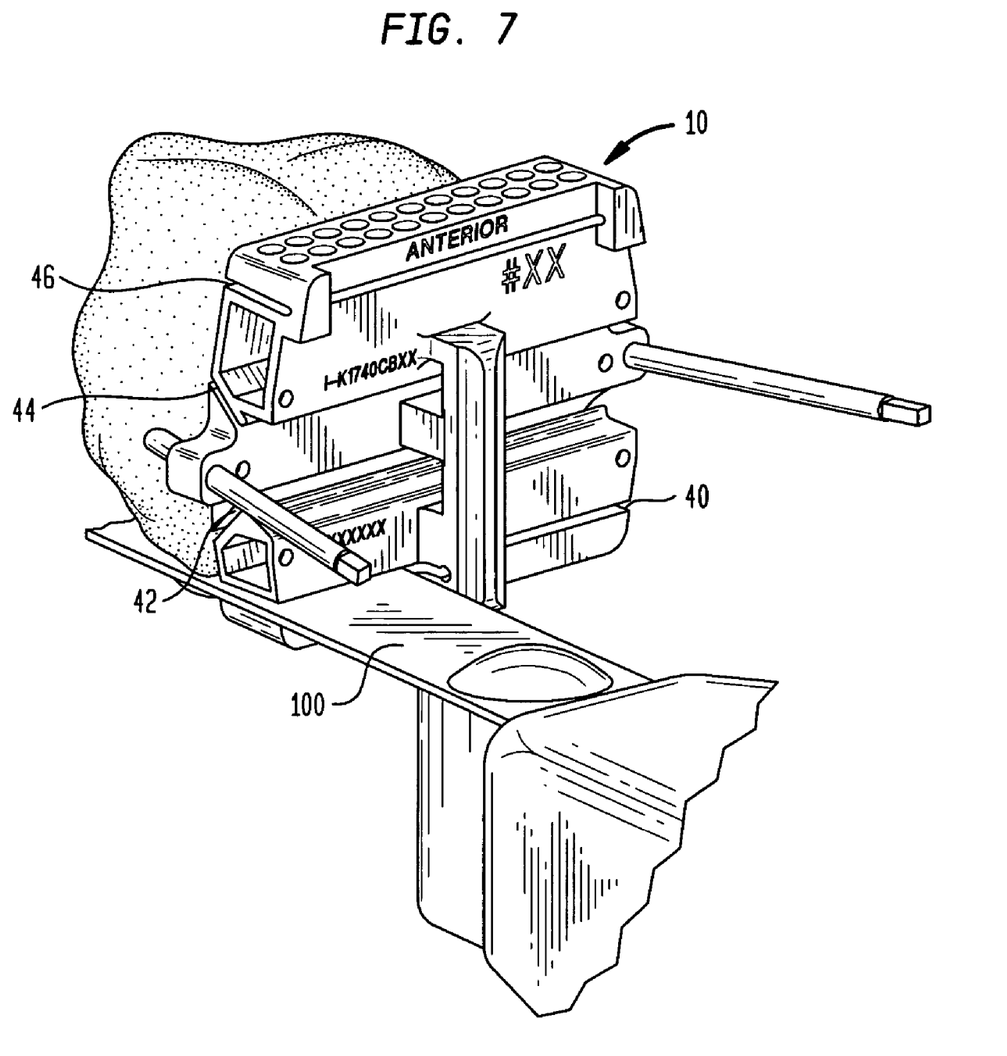
FIGS. 7, 8 and 9 are isometric views of the cutting block mounted on the distal femur showing a saw blade making an anterior cut, a posterior cut and an anterior chamfer cut respectively.
Figure 8:
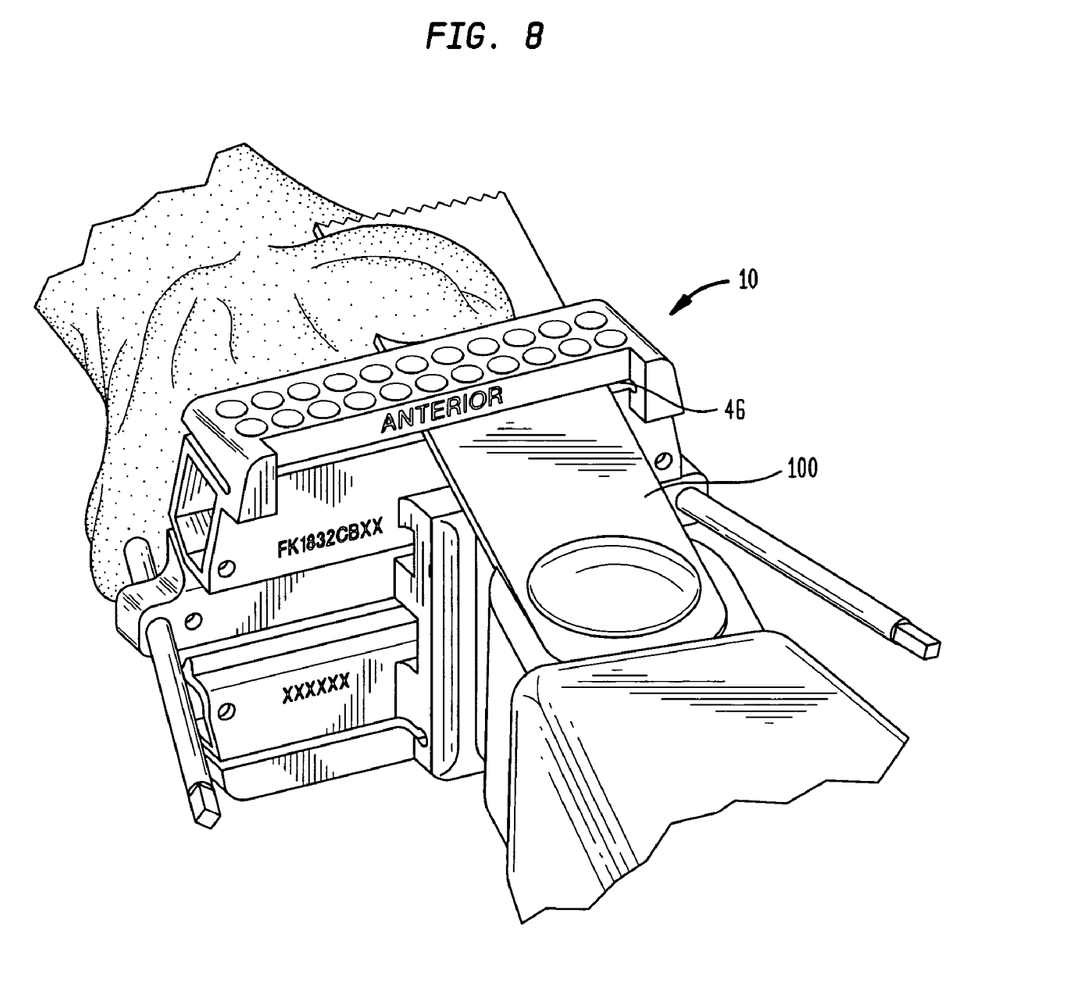
Figure 9:
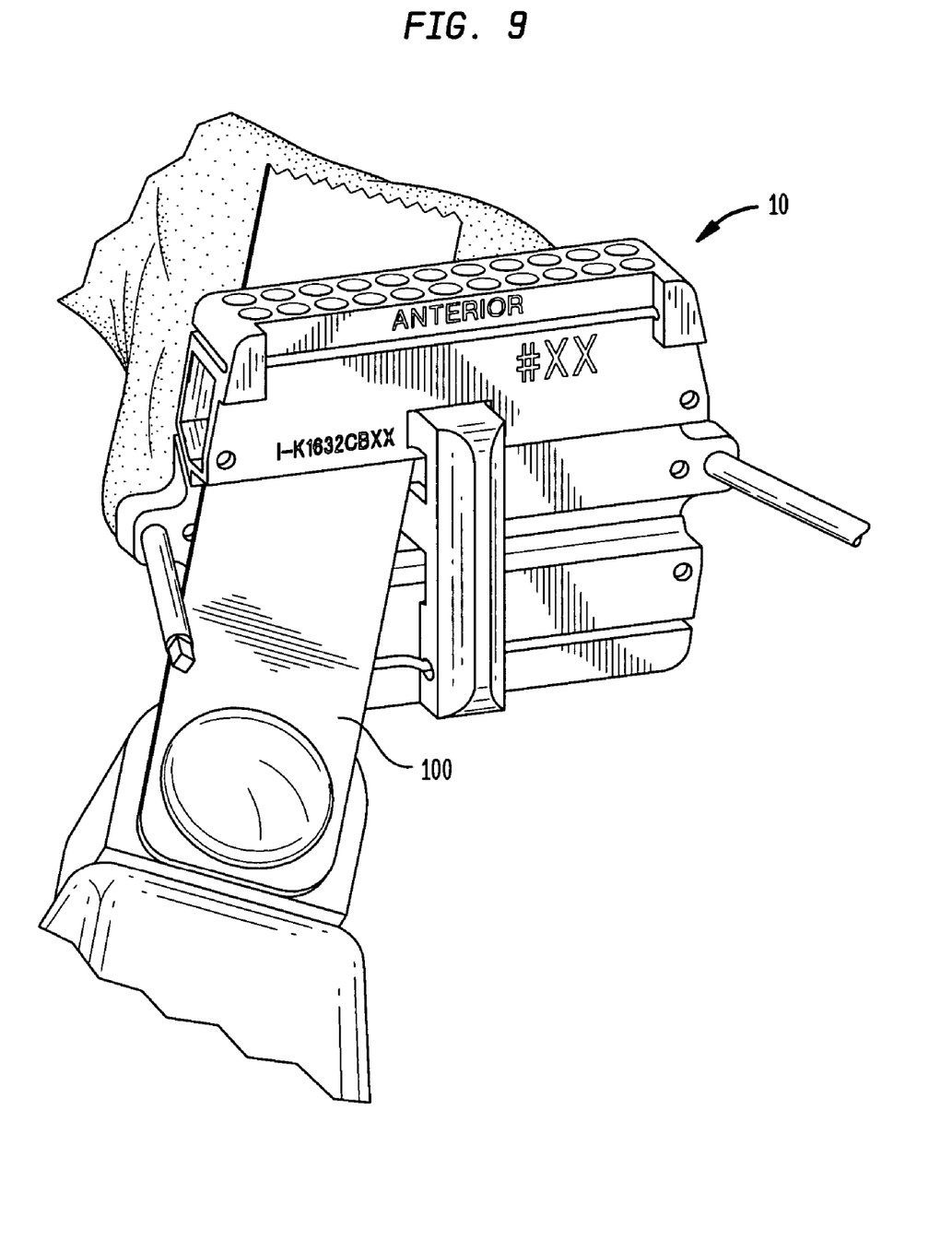

FIGS. 7, 8 and 9 show the cutting block 10 of the present invention being used with a typical oscillating saw blade 100. Since each of the slots 40, 42, 44, 46 are uninterrupted the blade 100 may be angled to completely form the resected surface of the distal femur.

The preferred manufacturing process for cutting block 10 now will be described. In the preferred manufacturing process, a block of surgical instrument materials such as stainless steel is provided. Initially, the distal surface, proximal/distal profile, peg holes and ventilation holes are machined using a 4-Axis CNC Mill. The distal surface and peg holes will be used for location in following operation. The proximal/distal profile can be machined in this step as well to maintain perpendicularity to the distal surface. The ventilation holes are machined at this time to prevent the formation of internal burrs.

After the initial machining, a 3-Axis Wire EDM (Electrical Discharge Machining) is used to cut the A/P profile of the cutting block. This may be accomplished by locating the distal surface and the peg holes. A 3-Axis CNC Mill could also be used to complete this operation.

Using the Wire EDM, the M/L profile of the cutting block is then cut again locating by using the distal surface and the peg holes. The guide slots are then machined in the cutting block. Since these are the critical features in the device, accuracy is enhanced if all of the slots are cut in the same setup. A 4-Axis CNC Mill is used to clean up all of the remaining material on the top of the cutting block, drill the fixation holes and engrave all required markings. Finally, the cutting block is debarred, heat treated, tumbled and passivity. The block is ready for packaging.

The use of a 4-Axis CNC machine and a 3-Axis Wire EDM requires a total of (4) machining setups to manufacture the cutting block. With a "traditional" design of cutting block, either multiple setups are required to machine the guide slots or a secondary assembly/welding operation is required. The method of the present invention also enhances the accuracy of the cutting block as all of the critical features are cut during the same Wire EDM operation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cutting block mountable on a distally facing surface of a femur for guiding a saw blade making bone cuts on the distal femur comprising:
a body having at least three sections spaced in an anterior-posterior direction, each section having a planar proximally facing surface for being placed adjacent to a distally facing femoral surface and a distally facing surface; and
a single rib integrally formed with said body and connecting said at least three sections, said rib centrally located between a medial side and a lateral side of the block and integral with said distally facing surface of each of said sections, said rib spacing said sections to form guide slots between a central section and adjacent first and second sections for receiving the saw blade, said rib having a proximally facing surface adjacent said guide slots between said central section and said adjacent first and second sections spaced distally from said distally facing surface of said sections to form a gap therebetween;
wherein said first and second sections each include a guide slot surface, a hollow interior forming a chamber, and a plurality of openings which connect said chamber to said guide slot surface; and
wherein said guide slot surfaces on said first and second sections are oriented at different angles with respect to the distally facing femoral surface.

2. The cutting block as set forth in claim 1 wherein said guide slots formed by said central section are at anterior-posterior angles to a proximal-distal direction of the femur for forming anterior and posterior chamfer cuts on the distal femur.

3. The cutting blocks as set forth in claim 2 further comprising a fourth section coupled to said rib and spaced posteriorly from said posterior most section to form a posterior saw blade guide slot for forming a posterior cut on said distal femur.

4. The cutting block as set forth in claim 3 wherein said anterior most section has an anterior saw blade guide slot for forming a resection on an anterior surface of the distal femur.

5. The cutting block as set forth in claim 1 wherein said first section is the anterior most section, said guide slot surface is located between said first section and said central section being adapted to form a resection on an anterior surface of the distal femur.

6. The cutting block as set forth in claim 1 wherein said proximally facing surfaces of each of said sections are coplanar.

7. The cutting block as set forth in claim 6 wherein said coplanar proximally facing surfaces are adapted to contact a planar resected distal surface of the femur.

8. The cutting block as set forth in claim 1 wherein said central section includes holes for receiving proximally extending pins for extending into the distal femur.

9. The cutting block as set forth in claim 1 wherein said proximally facing rib surface is spaced further from said distal surface of said central section than said distal surfaces of said first and second sections.

10. A cutting block for forming an anterior cut, posterior cut, anterior chamfer cut and a posterior chamfer cut on the distal femur comprising:
first, second and third body sections, each having a planar proximally facing bone contacting surface and a distally facing surface, said second section located between said first and third sections; and
a single rib integrally formed with each body section on said distally facing surfaces of each of said sections, said rib centrally located between a medial side and a lateral side of the block spacing said sections to form saw blade guide slots between said second section and adjacent first and third sections wherein said saw blade guide slots are uninterrupted from said medial side of said cutting block to said lateral side of said cutting block for the entire spacing between said proximally and distally facing surfaces thereof with said rib adjacent each saw blade guide slot having a proximally facing rib surface spaced from said distally facing surfaces of said first, second and third body sections to form a gap therebetween, said guide slots extending partially into said rib and terminating proximally of a distal end surface of said rib;
wherein said saw blade guide slots between the first and second sections and between the second and third sections are oriented at different angles with respect to the distal femur.

11. The cutting block as set forth in claim 10 wherein said guide slots are formed between said second section and said adjacent first and third sections at anterior-posterior angles to a proximal-distal direction of the femur for forming anterior and posterior chamfer cuts on the distal femur.

12. The cutting blocks as set forth in claim 11 further comprising a fourth section coupled to said rib and spaced posteriorly from said posterior most section to form a posterior saw blade guide slot for forming a posterior cut on said distal femur.

13. The cutting block as set forth in claim 11 wherein said first section is the anterior most section, said guide slot between said first section and said second section being adapted to form a resection on an anterior surface of the distal femur.

14. The cutting block as set forth in claim 10 wherein at least two of said sections have a cross-section defining a hollow interior defined on two sides by walls forming said saw blade guide slots.

15. The cutting block as set forth in claim 10 wherein said proximally facing surfaces of each of said first, second and third body sections are coplanar.

16. The cutting block as set forth in claim 15 wherein said coplanar proximally facing surfaces are adapted to contact a planar resected distal surface of the femur.

17. The cutting block as set forth in claim 10 wherein said second section includes holes for receiving proximally extending pins for extending into the distal femur.

18. The cutting block as set forth in claim 10 wherein said proximally facing rib surface is spaced further from said distal facing surface of said second section than said distal facing surfaces of said first and third sections.

19. The cutting block as set forth in claim 10 wherein said saw blade guide slots form uninterrupted saw blade guide surfaces.

20. The cutting block as set forth in claim 10 wherein said first and second sections each include a guide slot surface, a hollow interior forming a chamber, and a plurality of openings which connect said chamber to said guide slot surface.

21. A cutting block for forming an anterior cut, posterior cut, anterior chamfer cut and a posterior chamfer cut on the distal femur comprising:
    first, second and third body sections, each having a planar proximally facing bone contacting surface and a distally facing surface, said second section located between said first and third sections;
    a single rib integrally formed on said distally facing surfaces and centrally located between a medial side and a lateral side of the block, said rib spacing said sections to form a saw blade guide slot between said second section and said first and third sections, said guide slots extending partially into said rib and terminating proximally of a distal end surface of said rib;
    each of said body sections having at least one planar saw blade guide surface; and
    means for coupling the rib to said first, second and third sections, said means spacing said sections to form each of said saw guide slots, said guide slots having said planar saw guide surface on at least one side of said slot, said means for coupling spaced from said distally facing surface of said said first, second and third portions of said block to form a gap therebetween thereby leaving said planar cutting guide surface uninterrupted;
    wherein said saw blade planar guide surfaces between said first and second sections and said second and third sections are oriented at different angles with respect to the distal femur.

22. The cutting block as set forth in claim 21 wherein said guide slots are formed between said second section and said adjacent first and third sections at anterior-posterior angles to a proximal-distal direction of the femur for forming anterior and posterior chamfer cuts on the distal femur.

23. The cutting blocks as set forth in claim 22 further comprising a fourth section coupled to said rib and spaced posteriorly from said posterior most section to form a posterior saw blade guide slot for forming a posterior cut on said distal femur.

24. The cutting block as set forth in claim 22 wherein said first section is the anterior most section, said guide slot between said first section and said second section being adapted to form a resection on an anterior surface of the distal femur.

25. The cutting block as set forth in claim 21 wherein said first and second sections each include a saw blade guide surface on facing surfaces of the slot therebetween, a hollow interior forming a chamber, and a plurality of openings which connect said chamber to said guide slot surface.

* * * * *